United States Patent
Kohler et al.

(10) Patent No.: US 10,299,820 B2
(45) Date of Patent: May 28, 2019

(54) METHODS AND SYSTEMS FOR DISRUPTING CALCIFIED WALLS OF BIOLOGICAL CONDUITS AND CALCIFIED LESIONS THEREIN

(71) Applicant: Cardiovascular Systems, Inc., New Brighton, MN (US)

(72) Inventors: Robert E. Kohler, Lake Elmo, MN (US); Brad J. Martinsen, St. Louis Park, MN (US); Michael X. Yang, Maple Grove, MN (US); Yihao Zheng, Ann Arbor, MI (US); Albert Shih, Ann Arbor, MI (US); Rohit Deokar, Minneapolis, MN (US)

(73) Assignee: Cardiovascular Systems, Inc., New Brighton, MN (US)

( * ) Notice: Subject to any disclaimer, the term of this patent is extended or adjusted under 35 U.S.C. 154(b) by 283 days.

(21) Appl. No.: 15/047,174

(22) Filed: Feb. 18, 2016

(65) Prior Publication Data

US 2016/0242805 A1     Aug. 25, 2016

Related U.S. Application Data

(60) Provisional application No. 62/118,696, filed on Feb. 20, 2015, provisional application No. 62/134,408, (Continued)

(51) Int. Cl.
*A61B 17/22* (2006.01)
*A61B 17/32* (2006.01)
*A61B 17/3207* (2006.01)

(52) U.S. Cl.
CPC .......... *A61B 17/320068* (2013.01); *A61B 17/22012* (2013.01); *A61B 17/3207* (2013.01);
(Continued)

(58) Field of Classification Search
CPC .......... A61B 2017/22008; A61B 2017/22011; A61B 2017/22014; A61B 2017/22015; A61B 2017/22017; A61B 2017/22018
See application file for complete search history.

(56) References Cited

U.S. PATENT DOCUMENTS 8,597,313 B2 * 12/2013 Thatcher ........ A61B 17/320758
606/159

OTHER PUBLICATIONS

International Preliminary Report on Patentability, dated Aug. 22, 2017, for PCT Application No. PCT/US2016/018618, filed Feb. 19, 2016.

* cited by examiner

*Primary Examiner* — Martin T Ton
(74) *Attorney, Agent, or Firm* — Barnes & Thornburg LLP; Jeffrey R. Stone

(57) ABSTRACT

The present system is directed in various embodiments to rotational atherectomy systems and methods generally. More specifically, a method for methodically softening and disrupting calcification within the wall of a biological conduit or lumen. This result is achieved by use of at least one eccentric head that, during high-speed rotation within the exemplary lumen, produces a combination of a low-frequency orbital motion comprising a force that is exerted against the lumen wall, with concomitant deflection of same, and a high-frequency pulsatile frequency, also with concomitant exertion of force against the lumen wall and deflection of same. These force-driven deflections produce shockwaves within the layers of the exemplary artery's wall layers, resulting in systematic disruptions of any calcification within the intimal and/or medial layers of the subject artery. In addition, any calcification within the occlusion is also softened and disrupted, increasing compliance of the vessel and/or lesion.

4 Claims, 5 Drawing Sheets

Related U.S. Application Data filed on Mar. 17, 2015, provisional application No. 62/190,411, filed on Jul. 9, 2015.

(52) U.S. Cl.
CPC ............... *A61B 17/320758* (2013.01); *A61B 2017/22011* (2013.01); *A61B 2017/22051* (2013.01); *A61B 2017/320004* (2013.01); *A61B 2017/320766* (2013.01)

METHODS AND SYSTEMS FOR DISRUPTING CALCIFIED WALLS OF BIOLOGICAL CONDUITS AND CALCIFIED LESIONS THEREIN

CROSS-REFERENCE TO RELATED APPLICATIONS

This application claims priority to App. Ser. No. 62/118,696, entitled "Secondary Mechanism Of Action Of Orbital Atherectomy," filed Feb. 20, 2015; Appl. Ser. No. 62/134,408, entitled "Secondary Mechanism Of Action of Orbital Atherectomy," filed Mar. 17, 2015; and App. Ser. No. 62/190,411, entitled "Experimental Investigation Of The Abrasive Crown Dynamics In Orbital Atherectomy," filed Jul. 9, 2015, the entire contents of each of which are hereby incorporated by reference.

INVENTORS

Robert E. Kohler, a citizen of the United States, resident in Lake Elmo, Minn.

Brad J. Martinsen, a citizen of the United States, resident in St. Louis Park, Minn.;

Michael X. Yang, a citizen of the United States, resident in Maple Grove, Minn.;

Yihao Zheng, a citizen of the People's Republic of China, resident in Ann Arbor, Mich.;

Albert Shih, a citizen of the United States, resident in Ann Arbor, Mich.; and

Rohit Deokar, a citizen of India, resident in Minneapolis, Minn.

FIELD OF THE INVENTION

The present invention generally relates to methods and systems used for removing or modifying tissue from bodily passageways or conduits, such as removal and/or modification of atherosclerotic plaque from arteries, using a high-speed rotational atherectomy device. More specifically, the present invention relates to softening or otherwise disrupting calcification within a lesion and/or the intimal and/or medial wall layers of the passageway or conduit, e.g., an artery, using a combination of a low-frequency orbital motion and/or a high-frequency pulsatile frequency thereby increasing the compliance of the lesion and/or wall layers.

DESCRIPTION OF THE RELATED ART

Generally, various embodiments of the present invention comprise systems and methods for removing occlusions from biological or bodily conduits or lumens, e.g., an artery using rotational atherectomy. Various rotational atherectomy systems are known in the art.

For example, U.S. Pat. No. 5,314,438 (Shturman), incorporated herein in its entirety by reference, discloses an atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. This device is capable of opening an artery to a diameter about equal to the diameter of the enlarged abrading surface of the drive shaft since the enlarged abrasive section of the drive shaft is not eccentric.

U.S. Pat. No. 6,494,890 (Shturman) discloses a known atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

U.S. Pat. No. 5,681,336 (Clement) provides a known eccentric tissue removing burr with a coating of abrasive particles secured to a portion of its outer surface by a suitable binding material. This construction is limited, however because, as Clement explains at col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

Blood vessels comprise layers as is well known in the art. The innermost layer is the tunica intima, intima or intimal layer. Generally, rotational atherectomy devices and methods cut, sand and/or scrape occlusions that have built up along this intimal layer. The next layer of the blood vessel, working from the inside of the vessel out, is the tunica media, also referred to as the medial layer. Calcification can build up within this medial layer, as well as within the intimal layer. Simply cutting, sanding and/or scraping the interior surface of the intimal layer during high-speed rotational atherectomy does not treat, soften or disrupt calcification that has developed within the atherosclerotic plaque or lesion, and/or the intimal or medial layers.

Thus, a need exists in the art generally for devices, systems and methods to not only remove an occlusion from the interior surface of the intimal layer of a vessel, but also to treat, e.g., softening or otherwise disrupting, any calcification that has developed within the plaque or lesion, intimal and/or medial layers of the vessel with concurrent improvement in vessel compliance in the treated area. Note that this is a non-limiting example as the disclosed inventions may be used to treat and/or improve compliance of the plaque or lesion, and the bodily lumen or conduit walls by softening or otherwise disrupting the calcification that is located therein.

The present inventions address these, among other, needs.

BRIEF SUMMARY OF THE INVENTION

The present system is directed in various embodiments to rotational atherectomy, also referred to herein as orbital atherectomy, devices, systems and methods generally. More specifically, a method for methodically softening and otherwise disrupting calcification located within the atherosclerotic plaque, e.g., lesion or occlusion in a lumen, and/or the wall of a biological conduit or lumen. For example, calcification within the intimal and/or medial layer walls of a blood vessel, e.g., an artery, may be methodically softened or otherwise disrupted with various embodiments of the present invention. The softening and/or disruption of the calcification in the walls of the exemplary artery may be accomplished in conjunction with abrading removal of any occlusion located on the interior surface of the exemplary artery and, therefore, located within the artery's lumen. In certain embodiments, however, the eccentric head that is used is not an abrading head and may therefore be a smooth head lacking in abrasive coating.

The result achieved by use of at least one eccentric head, smooth or abrading, that, during high-speed rotation within the exemplary lumen, has for the first time been found to produce a combination of a low-frequency orbital motion comprising a force that is exerted against the lumen wall, with concomitant deflection of same, and a high-frequency pulsatile frequency, also with concomitant exertion of force against the lumen wall and deflection of same. These force-driven circumferential deflections produce a series of shockwaves within the layers of the exemplary artery's wall layers, resulting in systematic disruptions of any calcification within the intimal and/or medial layers of the subject artery. In addition, any calcification within the occlusion or lesion is also softened and disrupted. Thus, as this process proceeds, the compliance of the vessel, as well as the lesion itself, improves.

DETAILED DESCRIPTION

Figure 1:
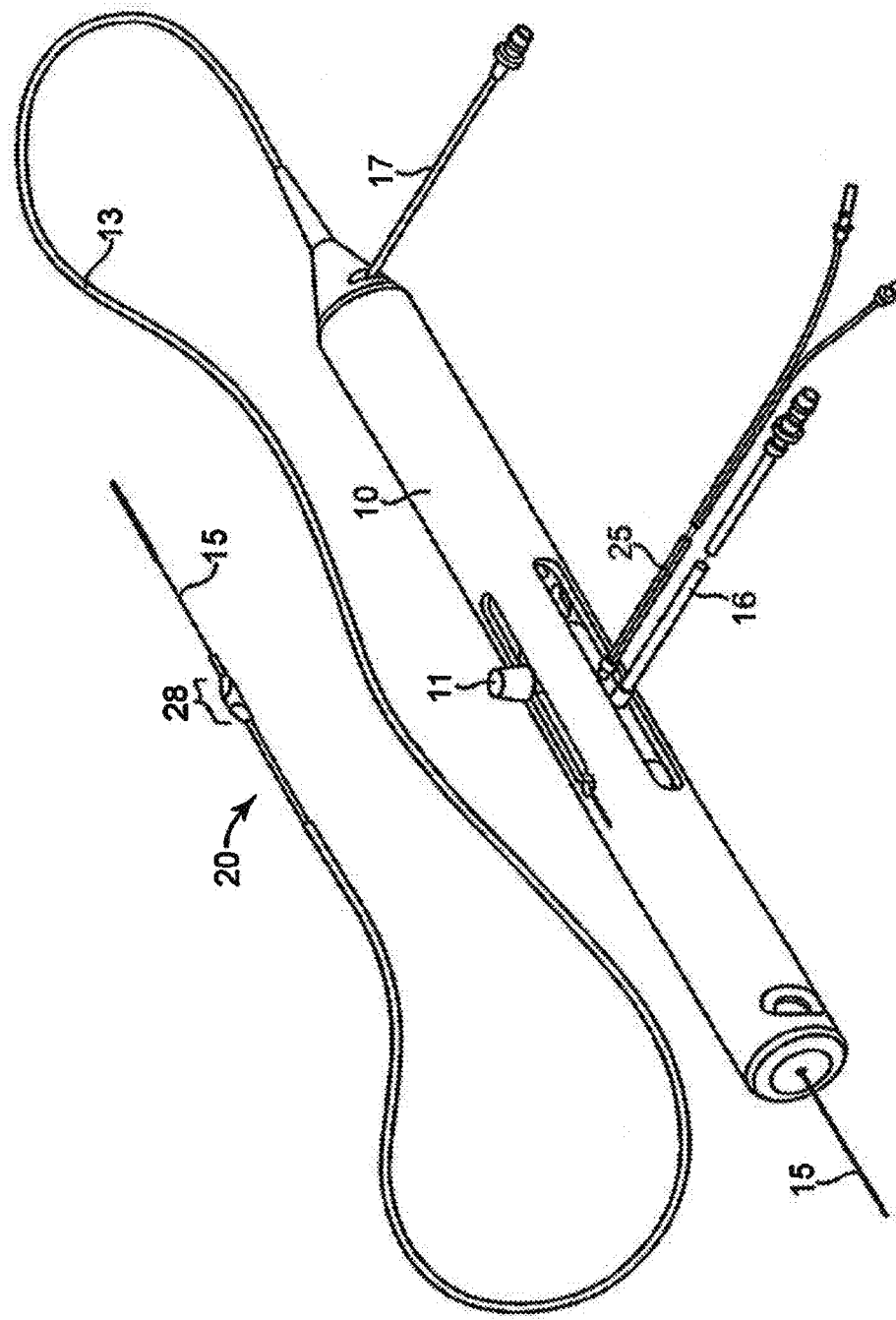
FIG. 1 illustrates a perspective view of a known rotational atherectomy device.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

The present invention provides systems, devices and methods comprising a high-speed rotational drive shaft with an eccentric abrading (or smooth and non-abrading) head, e.g., and within limitation, a crown or burr mounted thereon. FIG. 1 is a perspective view of a known rotational orbital atherectomy device. The device includes a handle portion 10, an elongated, flexible drive shaft 20 having an eccentric enlarged abrading head 28, and an elongated catheter 13 extending distally from the handle portion 10. The drive shaft 20 is constructed from helically coiled wire as is known in the art and the abrading head 28 is fixedly attached thereto. The catheter 13 has a lumen in which most of the length of the drive shaft 20 is disposed, except for the enlarged abrading head 28 and a short section distal to the enlarged abrading head 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism, e.g., an electric motor with associated control mechanisms) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20 (details regarding such handles and associated instrumentation are well known in the industry, and are described, e.g., in U.S. Pat. No. 5,314,407, issued to Auth, and incorporated by references herein in its entirety). The handle 10 also desirably includes a control knob 11 for advancing and retracting the turbine and drive shaft 20 with respect to the catheter 13 and the body of the handle.

The abrading head 28 in FIG. 1 is shown as an eccentric solid crown, attached to the drive shaft 20 near the distal end of the drive shaft 20. The term "eccentric" is used herein to denote that the center of mass of the crown is laterally displaced away from the rotational axis of the drive shaft 20. As the drive shaft rotates rapidly, the displaced center of mass of the crown causes the drive shaft to flex radially outward in the vicinity of the crown as it spins, so that the crown may abrade over a larger diameter than its own rest diameter. Eccentric solid crowns are disclosed in detail in, for example, U.S. patent application Ser. No. 11/761,128, filed on Jun. 11, 2007 to Thatcher et al. under the title, "Eccentric abrading head for high-speed rotational atherectomy devices", published on Dec. 11, 2008 as U.S. Patent Application Publication No. US2008/0306498, and incorporated by reference herein in its entirety.

The drive shaft, and eccentric abrading head, may be rotated at speeds within the range of 20,000 to 200,000 rpm. Thus, if the abrading head is at least partially covered or coated with an abrasive, e.g., diamond grit, it will enable smooth sanding of superficial and relatively resilient plaque formed on the interior surface of the intimal layer of the vessel or conduit. The abrading head may comprise cutting blades or other known means and mechanisms for removing this interior plaque, leaving behind a smoothed surface. In other embodiments, a smooth, non-abrading head may be used. In this case, there will be no abrading and the effect will be the softening and/or disrupting of soft tissue and/or calcification within a lesion and/or the wall of the subject conduit as a result of the forces and energy waves described herein.

Although not wishing to be constrained to any particular theory of operation, applicants have observed that offsetting the center of mass of the abrading head radially away from the drive shaft's rotational axis also produces an "orbital" movement of the eccentric abrading head in addition to the high-speed rotation of the rotating abrading (or non-abrading smooth) head. The diameter of the "orbit" traversed by the abrading head during high-speed rotation is limited first by the internal diameter of the biological conduit or lumen, e.g., a blood vessel.

Thus, "eccentric" or "eccentricity" of the eccentric head is defined herein as a radial offsetting of the center of mass of the eccentric head away from the rotational axis of the drive shaft to which the eccentric head is attached or otherwise disposed on. This radial offsetting may be achieved with a geometrically eccentric, i.e., asymmetric, structure. Alternatively, a symmetric and geometrically concentric structure may be eccentric by use of materials of differing densities in the eccentric head, or by creating hollow areas within the eccentric head in order to radially offset the center of mass away from the drive shaft's rotational axis.

The diameter of the eccentric head's orbit is also dependent upon the rotational speed of the drive shaft and the abrading head attached thereto as well as by the mass of the abrading head. Therefore, the orbit's diameter is controllable by varying the drive shaft's rotational speed, and therefore the rotational speed of the eccentric head, as well as by varying the mass of the eccentric abrading head.

The eccentric head's orbit is dependent upon its rotational speed and mass because the subject conduit or lumen wall is susceptible to pressured deflection caused by the impact of the eccentric head and the centrifugal force generated thereby during rotation. The centrifugal force of the rotating eccentric head may be determined as follows and as the skilled artisan will readily understand:

$$F_c = mv^2/R, \text{ where } m=\text{mass}, v=\text{velocity and } R=\text{radius}.$$

The centrifugal force of the mass of a typical eccentric head during rotation may range from 0.00 to 5.00 N depending on the mass of the abrading head and the speed of its rotation.

Figure 2A:
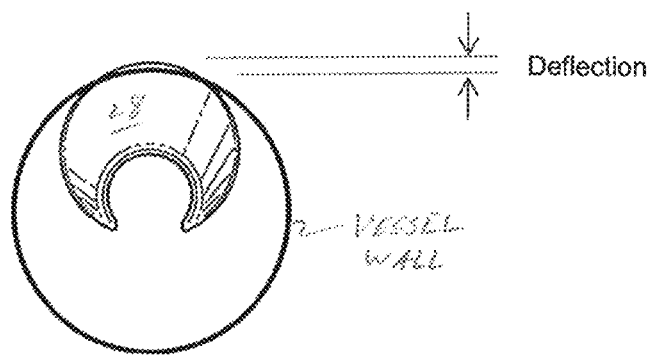
FIG. 2A illustrates a cutaway view of one embodiment of the present invention.
Figure 2B:
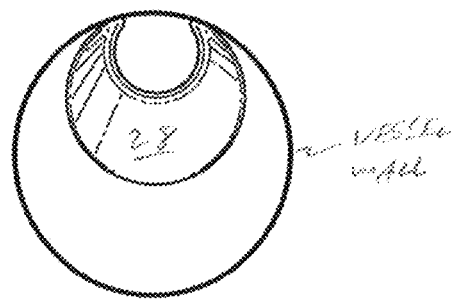
FIG. 2B illustrates a cutaway view of one embodiment of the present invention.

In addition, because of the head is eccentric, it will also generate a cyclic, pulsatile or alternative force that repeatedly presses to create pressure against the vessel wall and, if the pressure force is sufficiently large, the vessel wall will deflect outward away from the vessel lumen. This cyclic force may also deflect any remaining plaque still attached to the vessel wall. See FIG. 2A for illustration of the case where the impact force of the abrading head 28 (shown without drive shaft) is sufficiently large to cause an outward radial deflection of the vessel wall. FIG. 2B illustrates the case wherein the impact force of the abrading head 28 is not large enough to cause the vessel wall to deflect.

As will be further described below, Applicants have discovered that the relevant performance characteristics of the high-speed rotating eccentric head comprise (1) a rotational speed (rpm), resulting in a high-speed frequency pulsatile or cyclic rotation (Hz); and (2) a low-frequency orbit (Hz), also cyclic in nature. Typical orbital atherectomy rotational speeds of 60,000, 90,000, and 120,000 rpm in an exemplary 4.8 m diameter vessel have been observed to produce abrading head motion combination of: (1) a high speed frequency rotation of approximately 1,000, 1,500, and 1,800 Hz; and (2) a corresponding low-frequency orbit of approximately 18, 38 and 40 Hz. Other combinations will readily present themselves to the skilled artisan, dependent upon a number of factors, including, but not limited to, the mass of the eccentric head and its rotational speed.

Figure 3:
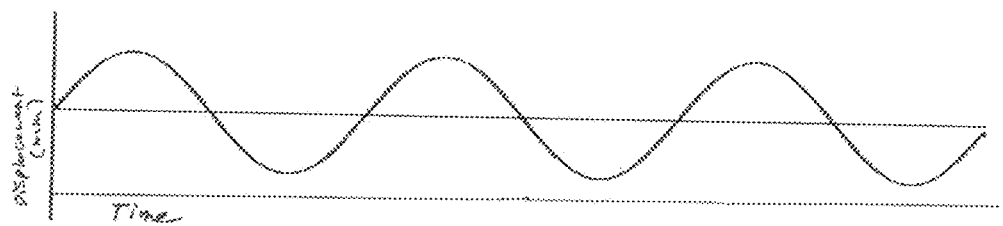
FIG. 3 illustrates a low-frequency, large amplitude motion of one embodiment of the present invention.
Figure 4:
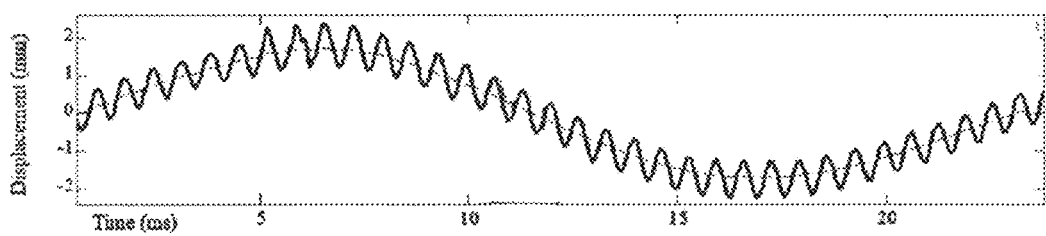
FIG. 4 illustrates a high-frequency, small amplitude motion, superimposed upon a low-frequency, large amplitude motion, of one embodiment of the present invention.

FIG. 3 illustrates the low-frequency, large amplitude motion of the eccentric head during high-speed rotation. FIG. 4 illustrates the high-frequency, small amplitude pulsatile frequency of the rotating eccentric head, superimposed upon the low-frequency, large amplitude motion of the rotating head.

These motions create a circumferential cyclical force loading and unloading on the lesion as well as the conduit or lumen, e.g., arterial, wall creates disruption in the plaque or lesion on the interior surface of the intima, as well as disruption and softening of an calcification formed within the intimal and/or medial layers. It will now be understood by the skilled artisan that as the eccentric head rotates, a cyclical strain loading and off-loading on the exemplary vessel wall is produced. The frequency of the cyclical strain loading and off-loading may range from 100 to 10,000 Hz, depending on the rotational speed of the drive shaft and eccentric head. The magnitude of the cyclical strain force produced in this case depends on the rotational speed and the mass of the rotating eccentric head as well as the location of the center of mass which will be located radially away from the rotational axis of the drive shaft. We will refer to the eccentric head infra as an eccentric abrading head for simplicity, though it is to be understood that the eccentric head may be non-abrading as well.

This cyclical strain force, in turn, creates shockwaves of energy through the vessel wall, including the intimal and medial layers, as well as through the lesion. As the eccentric abrading head rotates, the cyclical or pulsatile strain force is delivered circumferentially around the interior surface of the vessel wall. The skilled artisan will now also recognize that the cyclical or pulsatile strain force may be produced by non-mechanical means, e.g., generated by vibrational, ultrasonic or other pulsatile energy frequency generators, e.g., a pulsatile balloon capable of circumferential delivery of pulsatile energy to the plaque or lesion and/or vessel or conduit wall.

As a result, a combination of low-frequency and/or high-frequency forces is generated at the lesion and/or the vessel wall. These low-frequency and high-frequency forces produce related energy waves that travel through the lesion and at least the intimal and medial layers of the vessel wall, causing softening and/or disrupting of any calcification formed therein.

By sanding the interior surface of the vessel wall free of occlusive material, e.g., plaque, and in combination also disrupting any existing calcification within the lesion and/or intimal and/or medial layers of the exemplary vessel, the vessel is better prepared for adjunctive therapies, e.g., angioplasty including drug-coated balloons, stenting, biovascular scaffolding, and other means of introducing, e.g., anti-restenosis or other therapeutic agents to the treatment region.

Another key effect of the cyclical or pulsatile strain force loading on the vessel wall described herein is to pre-treat the calcification within the intimal and/or medial layers to ensure better absorption of any therapeutic agents. Another effect is to increase the compliance of the exemplary vessel and the lesion in the treatment region as a result of disrupted or otherwise softened calcification deposits or formations, allowing the vessel and lesion to be more flexible.

Various embodiments of the present inventions may be practiced using a rotational atherectomy system as described generally in U.S. Pat. No. 6,494,890, entitled "ECCENTRIC ROTATIONAL ATHERECTOMY DEVICE," which is incorporated herein by reference. Additionally, the disclosure of the following co-owned patents or patent applications are herein incorporated by reference in their entireties: U.S. Pat. No. 6,295,712, entitled "ROTATIONAL ATHERECTOMY DEVICE"; U.S. Pat. No. 6,132,444, entitled "ECCENTRIC DRIVE SHAFT FOR ATHERECTOMY DEVICE AND METHOD FOR MANUFACTURE"; U.S. Pat. No. 6,638,288, entitled "ECCENTRIC DRIVE SHAFT FOR ATHERECTOMY DEVICE AND METHOD FOR MANUFACTURE"; U.S. Pat. No. 5,314,438, entitled "ABRASIVE DRIVE SHAFT DEVICE FOR ROTATIONAL ATHERECTOMY"; U.S. Pat. No. 6,217,595, entitled "ROTATIONAL ATHERECTOMY DEVICE"; U.S. Pat. No. 5,554,163, entitled "ATHERECTOMY DEVICE"; U.S. Pat. No. 7,507,245, entitled "ROTATIONAL ANGIOPLASTY DEVICE WITH ABRASIVE CROWN"; U.S. Pat. No. 6,129,734, entitled "ROTATIONAL ATHERECTOMY DEVICE WITH RADIALLY EXPANDABLE PRIME MOVER COUPLING"; U.S. Pat. No. 8,597,313, entitled "ECCENTRIC ABRADING HEAD FOR HIGH-SPEED ROTATIONAL ATHERECTOMY DEVICES"; U.S. Pat. No. 8,439,937, entitled "SYSTEM, APPARATUS AND METHOD FOR OPENING AN OCCLUDED LESION"; U.S. Pat. Pub. No. 2009/0299392, entitled "ECCENTRIC ABRADING ELEMENT FOR HIGH-SPEED ROTATIONAL ATHERECTOMY DEVICES"; U.S. Pat. Pub. No. 2010/0198239, entitled "MULTI-MATERIAL ABRADING HEAD FOR ATHERECTOMY DEVICES HAVING LATERALLY DISPLACED CENTER OF MASS"; U.S. Pat. Pub. No. 2010/0036402, entitled "ROTATIONAL ATHERECTOMY DEVICE WITH PRE-CURVED DRIVE SHAFT"; U.S. Pat. Pub. No. 2009/0299391, entitled "ECCENTRIC ABRADING AND CUTTING HEAD FOR HIGH-SPEED ROTATIONAL ATHERECTOMY DEVICES"; U.S. Pat. Pub. No. 2010/0100110, entitled "ECCENTRIC ABRADING AND CUTTING HEAD FOR HIGH-SPEED ROTATIONAL ATHERECTOMY DEVICES"; U.S. Design Pat. No. D610258, entitled "ROTATIONAL ATHERECTOMY ABRASIVE CROWN"; U.S. Design Pat. No. D6107102, entitled "ROTATIONAL ATHERECTOMY ABRASIVE CROWN"; U.S. Pat. Pub. No. 2009/0306689, entitled "BIDIRECTIONAL EXPANDABLE HEAD FOR ROTATIONAL ATHERECTOMY DEVICE"; U.S. Pat. Pub. No. 2010/0211088, entitled "ROTATIONAL ATHERECTOMY SEGMENTED ABRADING HEAD AND METHOD TO IMPROVE ABRADING EFFICIENCY"; U.S. Pat. Pub. No. 2013/0018398, entitled "ROTATIONAL ATHERECTOMY DEVICE WITH ELECTRIC MOTOR"; and U.S. Pat. No. 7,666,202, entitled "ORBITAL ATHERECTOMY DEVICE GUIDE WIRE DESIGN." It is contemplated by the inventions described herein that the features of one or more of the embodiments of the present inventions may be combined with one or more features of the embodiments of systems, devices and methods described therein.

Working Example 1

The following working example investigates the motion and contact forces of an eccentric abrading during high-speed orbital atherectomy. A high-speed camera and image processing technique were utilized to visualize and quantify the crown motion and its interaction with the wall of a transparent arterial phantom made of tissue-mimicking polyvinyl chloride (PVC). Forces were measured simultaneously by a piezoelectric force dynamometer with sufficient sensitivity and bandwidth for such rapid dynamic measurements.

Materials and Methods

The experimental setup consisted of three modules—the atherectomy device, an arterial phantom, and the measurement system—in the following sections.

Atherectomy Device

The orbital atherectomy device in Working Example 1 is the Diamondback 360® manufactured by Cardiovascular Systems Inc. (St. Paul, Minn.), assignee of the present disclosure and is similar to the device illustrated in FIG. 1. This device consists of three units: (1) a motor and control unit, (2) a catheter, and (3) saline and a saline pump as is well known in the art. The motor and control unit includes an electric motor and a set of speed selection buttons to generate three rotational speeds: 60,000, 90,000 and 120,000 rpm.

Arterial Phantom

The arterial phantom meant to simulate the artery and flow of blood consists of (1) a tissue-mimicking phantom, (2) a blood-mimicking water source, (3) a PVC tube connecting the phantom and water source, and (4) force isolators between the PVC tube and the tissue phantom.

The transparent tissue-mimicking phantom consisted of a PVC vessel and muscle phantom and a square polycarbonate (PC) tube to encase the soft material. Its geometry was designed to mimic the human proximal popliteal artery region, one of the most common locations of lower extremity atherosclerosis [20]. To measure the force during the procedure, the outer square PC tube (50.8 mm outer width, 2.03 mm wall thickness, and 150 mm length) was mounted to a piezoelectric dynamometer (Model 9256-C by Kistler) via a custom fixture. Inside the tube were the PVC vessel and muscle phantoms. The vessel phantom, to accommodate the proximal popliteal artery's elastic properties and anatomy, was made of soft PVC (45 kPa elastic modulus) and had a 4.8 mm inner diameter and a 2.0 mm wall thickness. The muscle phantom surrounded the vessel phantom and bounded by the outer PC tube was made of PVC with a lower elastic modulus (about 8 kPa).

To fabricate the tubular vessel phantom, a 4.76 mm diameter aluminum rod was dipped into PVC plastisol (M-F Manufacturing Co., Fort Worth, Tex.) heated to 150° C. for 20 min and degassed in a vacuum chamber at −90 kPa for 10 min. To make the muscle phantom, the PVC plastisol was mixed in a 1:1 ratio with a softener and poured into the space between the vessel phantom (supported by the aluminum rod) and the square encasing tube. After the PVC was cooled to room temperature and cured, the aluminum rod was removed. The inner diameter of the vessel phantom became 4.8 mm after cooling as a result of the PVC shrinkage.

The blood mimicking water source was raised 1 m above the rest of the experimental setup, as shown in FIG. 2, to force the water to flow through the PVC tube and the tissue phantom at a flow rate of 1.3 L min$^{-1}$. The PVC tube (ID of 6.35 mm, wall thickness of 1.59 mm, and 1.7 m in length) had a 0.7 m long horizontal section in the X direction connected to the tissue phantom and a vertical section in the Z direction connected to the blood mimicking water source. A 1.5 mm diameter hole was drilled into the PVC tube to allow the catheter to enter the horizontal section and access the tissue phantom.

Force isolators were implemented on both sides of the tissue phantom to isolate the forces on the PVC tube induced by the vibration of the catheter. The isolators were individually made of two round polyethylene terephthalate (PETG) tubes (7.94 mm OD and 4.76 mm ID) connected by wrapping the Teflon tape.

Measurement System

Two key devices were used in this study to measure the eccentric head dynamics operating within the phantom during high-speed rotation: (1) a high speed camera (Model FASTCAM-1024PCI by Photron); and (2) a force dynamometer. The camera was used to image the crown (through the transparent phantom) from the side or the front to record the crown motion. Recording at 18,000 frames per second (fps) allowed a minimum of 9 frames to be captured for each revolution of the crown even at its highest rotational speed setting of 120,000 rpm. A fiber optic light source (Model 8375 by Fostec) was used to deliver a bright, concentrated light necessary for proper image quality. The dynamometer was mounted under the tissue phantom, and measured the force in the Y and Z directions (FIG. 2) at a sampling rate of 5,000 Hz. The Y- and Z-axis natural frequencies of this dynamometer (5,500 and 5,600 Hz [23]) were well above 2,000 Hz, the frequency experienced at the 120,000 rpm crown rotational speed.

Design of Experiment

For each individual test, video and force data collection began 10 s after powering the device up and lasted for 5 s. Five tests were conducted for each crown rotational speed (60,000, 90,000, and 120,000 rpm). The mean and standard deviation (SD) of the results from each of these five repeated tests at the three rotational speeds were calculated.

Working Example 1 Results

The eccentric abrading head motion was demonstrated for the first time to be a combination of high-frequency rotational forces and low-frequency orbiting forces applied circumferentially around the vessel lumen. The measured forces confirmed these rotational and orbital frequencies observed in the crown motion. Results from the three crown rotational speeds (60,000, 90,000, and 120,000 rpm) are presented in Tables 1 and 2 and the analysis of the crown dynamics at 90,000 rpm is here illustrated as an example.

TABLE 1

| Rotational Speed (rpm) | Frequency | Mean (Hz) | SD (Hz) |
| --- | --- | --- | --- |
| 60,000 | Rotational (high) | 1003.4 | 8.5 |
| | Orbital (low) | 19.3 | 0.6 |
| 90,000 | Rotational | 1499.6 | 3.0 |
| | Orbital | 38.2 | 1.7 |
| 120,000 | Rotational | 0.4 | — |
| | Orbital | 40.5 | |

Rotational (high) and orbital (low) frequencies in abrading head motion at 3 rotational speeds.

Eccentric Head Motion

The high-frequency and small amplitude cyclical displacement of a designated point on the eccentric abrading head when rotated at 90,000 rpm is as shown in FIG. 4. FIG. 3 illustrates the low-frequency, large amplitude orbital motion frequency of the same eccentric abrading head during high-speed rotation. Additionally, FIG. 4 superimposes the small-amplitude high-frequency motion upon a large-amplitude low-frequency motion to enable viewing of the combination of low-frequency motion and high-frequency motion of the eccentric abrading head at high rotational speeds.

The mean and SD of the rotational and orbital frequencies of the eccentric abrading head motion in the five tests at three rotational speeds (60,000, 90,000, and 120,000 rpm) are summarized in the Table 1. Measured rotational frequencies of 1,003 and 1,500 Hz matched the rotational speed settings for 60,000 and 90,000 rpm, respectively. At 120,000 rpm, the instability of the eccentric abrading head rotational speed caused this value to range from 1,660 to 1,870 Hz (corresponding to 99,600 to 111,200 rpm) and is likely due to limitations of the driving motor. The eccentric abrading head orbital frequency in the vessel lumen for each rotational speed was 19.3, 38.2, and 40.5 Hz.

Contact Force

Figure 5B:
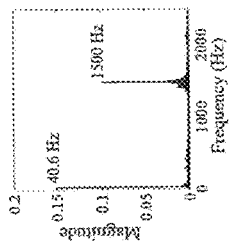
FIG. 5B illustrates the dominant frequencies illustrated in FIG. 5A.
Figure 5D:
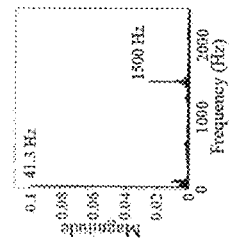
FIG. 5D illustrates the dominant frequencies illustrated in FIG. 5C.
Figure 5A:
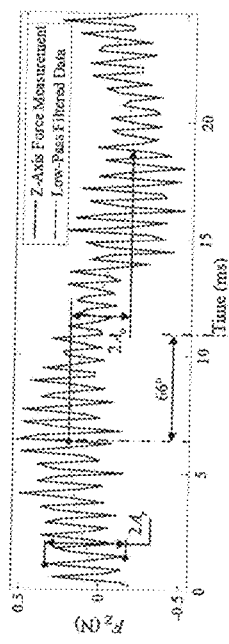
FIG. 5A illustrates force in the Z-axis direction for one embodiment of the present invention.
Figure 5C:
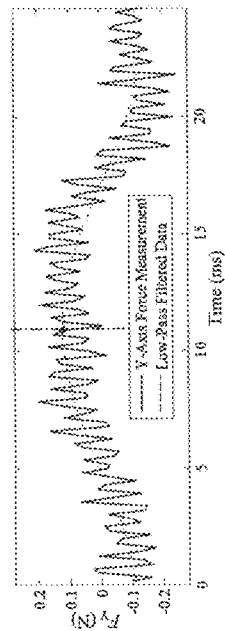
FIG. 5C illustrates force in the Y-axis direction for one embodiment of the present invention.

FIG. 5A shows the measured force in the Z–($F_Z$) and FIG. 5C illustrates the measured force in the Y-direction ($F_Y$) for one orbital period (24.4 ms) at the 90,000 rpm rotational speed. FIGS. 5B and 5D illustrate the two dominant frequencies observed. The combination of high and low frequencies described above is clearly illustrated in FIGS. 5A and 5C with a high-frequency, low-amplitude force superimposed over a low-frequency, high-amplitude force. The two dominant frequencies observed were 1,500 and 40.6 Hz for $F_Z$ and 1,500 and 41.3 Hz for $F_Y$ as provided in FIGS. 5B and 5D.

The amplitudes of a representative rotational and orbital frequency period are marked as $A_r$ and $A_O$, respectively, in FIG. 8(a). The force $F_Z$ can be represented as:

$$F_Z = A_r \sin(2p f_r t) + A_o \sin(2p f_o t)$$

where t is the time, $f_r$ and $f_o$ are the rotational and orbital frequencies, and $A_r$ and $A_o$ are the average amplitudes of the force components in the Z-direction in the rotational and orbital frequency, respectively. Adding $A_r$ and $A_o$ gives the average peak force, $F_{peak}$. The same analysis is repeated for $F_Y$. Table 2 summarizes the mean and SD of $f_r$, $f_o$, $A_r$, and $A_o$ for the five repeated tests and $F_{peak}$ at the three rotational speeds for $F_Z$ and $F_Y$. The $A_r$ and $A_o$ were the highest at a rotation speed of 90,000 rpm, with the $A_r$ and $A_o$ at 120,000 rpm close to those at 90,000 rpm and higher than those of 60,000 rpm. The $A_r$ and $A_o$ in the Z-direction were found to be higher than those in the Y-direction, possibly due to the effects of gravity and the dynamic response of the soft tissue phantom.

The measured forces at three rotational speeds (60,000, 90,000 and 120,000 rpm) are summarized in Table 2 below.

TABLE 2

| Rotational Speed (rpm) | Direction | $f_r$ (HZ) Mean (SD) | $A_r$ (N) Mean (SD) | $f_o$ (Hz) Mean (SD) | $A_o$ (N) Mean (SD) | $F_{peak}$ (N) |
| --- | --- | --- | --- | --- | --- | --- |
| 60,000 | Z | 1006.4 (12.4) | 0.074 (0.001) | 19.5 (0.9) | 0.025 (0.002) | 0.099 |
| | Y | 993.5 (4.3) | 0.086 (0.009) | 19.4 (1.0) | 0.018 (0.001) | 0.104 |
| 90,000 | Z | 1500.2 (0.4) | 0.255 (0.014) | 38.1 (1.3) | 0.169 (0.010) | 0.424 |
| | Y | 1500.2 (0.4) | 0.111 (0.011) | 38.3 (1.7) | 0.100 (0.013) | 0.211 |
| 120,000 | Z | 1637-1927 | 0.202 (0.007) | 40.5 (0.4) | 0.116 (0.007) | 0.318 |
| | Y | 1645-1903 | 0.117 (0.002) | 40.7 (0.3) | 0.093 (0.002) | 0.210 |

Force measurement at three rotational speeds.

Analysis and Comparison of $f_r$ and $f_o$ Measured Based on Image and Force

At 60,000 and 90,000 rpm, the values off, in Tables 1 and 2 are very close. At 120,000 rpm, $f_r$ varied within a similar range without a conclusive value for comparison. For $f_o$, the image-based measurements (19.3, 38.2, and 40.5 Hz in Table 1) were almost equal to those in Table 2 for $F_Y$ (19.5, 38.1, and 40.5 Hz) and $F_Z$ (19.4, 38.3, and 40.7 Hz) with less than 1% discrepancy, possibly as a result of the different sampling frequencies and the accompanying signal processing done for each method. The value off, results from the abrading head's orbiting centrifugal force. A linear relationship between $f_o$ and $\ln(A_o)$ is observed with R-square values of 0.92 and 0.98 for $F_Z$ and $F_Y$, respectively, at three rotational speeds, confirming the quadratic relationship of the eccentric abrading head's orbital frequency to its centrifugal force.

Heat Dispersion and Plaque Stress Softening

The abrading head's orbital motion may also reduce the heat accumulation and tissue thermal injury. Abrasive sanding is an energy intensive process and temperature rise can cause blood coagulation and tissue thermal injury during atherectomy. Due to the combination of rotational and orbital motions of the eccentric abrading head, no specific region of the vessel continuously contacts the crown. Such characteristic behavior of the eccentric abrading head's motion may be exploited to aid in heat dispersion.

Cyclic loading on the vessel could also help with the procedure by softening the plaque tissue, similar to the Mullin's Effect in rubber softening. In orbital atherectomy, or other systems designed to deliver the required vibrational and/or pulsatile forces contemplated herein, the lesion and vessel wall undergoes cyclic loading and unloading due to the crown's orbital motion. The eccentric abrading head's rotational motion contributes additional cyclic loading and unloading, elevating the local stress and further enhancing the stress softening of any calcified formations within the lesion or the vessel wall, e.g., the intimal and medial layers. This pulsatile force into the tissue may increase the compliance of the lesion and the vessel wall, facilitating higher rates of success in angioplasty, dispersion and tissue softening, including disruption of calcified deposits.

Figure 6:
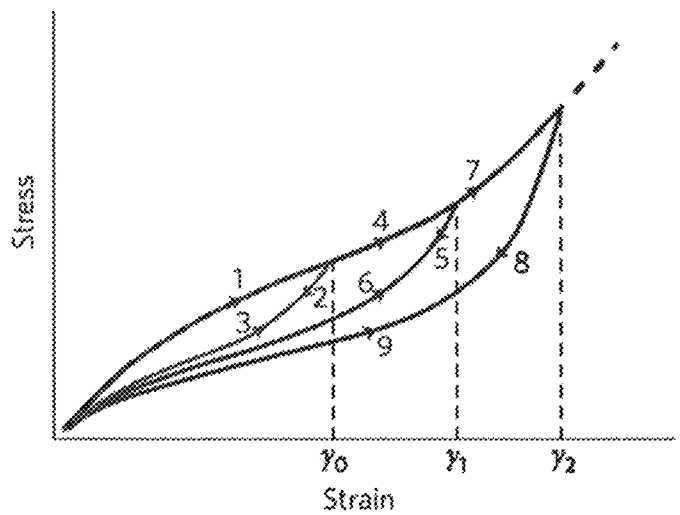
FIG. 6 illustrates a graph of Stress vs. Strain according to one embodiment of the present invention.
Figure 7:
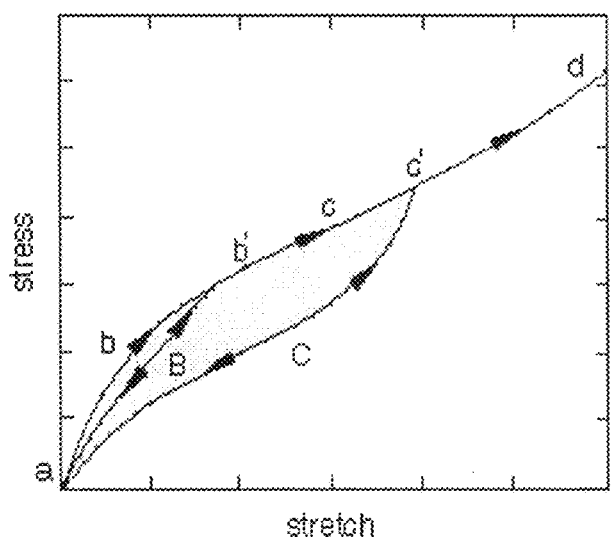
FIG. 7 illustrates a damage energy graph illustrating, inter alia, the Mullins Effect according to one embodiment of the present invention.

Thus, the softening disruption of soft tissues as well as calcified lesions and/or calcified intimal and/or medial layers of an arterial wall is an effect provided by the present invention. It is known that soft tissues undergo damage during progressive loading and unloading cycles. As can be seen in FIGS. 6 and 7, the loading and unloading take different paths and reloading occurs along the same path as previous unloading, up to the point of maximum previous loading. Significantly, softening according to the Mullin's Effect, only occurs once loading at a magnitude occurs that is more than the maximum previous load. The damage energy graphic of FIG. 7 illustrates this phenomenon.

CONCLUSIONS

This work has, for the first time, revealed an important element of eccentric abrading head dynamics in orbital atherectomy, namely that the eccentric abrading head rotates along its axis and orbits around the vessel axis and that this motion results in the rotational and orbital frequencies in the contact forces between the crown and vessel, which may facilitate heat Accordingly, one embodiment of the present invention comprises generating low-frequency and high-frequency circumferential forces within an exemplary artery. In some embodiments, one or both of these forces will be sufficiently large to cause a deflection in the lesion within the arterial lumen and/or within the arterial wall. In turn, low-frequency energy waves and high-frequency energy waves are generated within the lesion and/or arterial wall, including but not limited to the intimal and medial layers as is cyclic strain loading and unloading. In certain embodiments, the low-frequency and high-frequency circumferential forces remain at constant magnitudes. In other embodiments, the low-frequency and/or high-frequency forces are increased at least once during a treatment procedure in order to maximize the softening disruption of calcified deposits in the lesion and/or arterial wall according to the Mullin's Effect.

One outcome or result of the present invention comprises an increase in lesion and/or conduit or lumen, e.g., arterial, compliance. Compliance in this sense is defined as the ratio of the change of Area or Volume over the change of pressure. In vivo, compliance is calculated as the change in area of the lumen of an artery, e.g., between the systolic and diastolic pressures. Because any formed calcification within the arterial wall will be softened and disrupted by the presently described invention, the arterial wall compliance will also increase, becoming more flexible and less stiff. Thus, one significant focus of the present invention is to improve or increase the compliance of the treated lesion and/or conduit or lumen, e.g., an artery.

Yet another outcome of the present invention is that the method as described herein, e.g., orbital atherectomy done at a high-rotational speed with an eccentric abrading head, results in a smoothly-sanded, lesion-free lumen as well as softened and/or disrupted calcification within the intimal and/or medial layers of the arterial wall. This combination of circumstances allows, in turn, improved efficacy for adjunctive processes as described above. In particular, absorption of therapeutic agents, e.g., anti-restenosis agents, into the intimal and/or medial layers of the arterial wall as a result of the softening and/or disruption of any calcification formed therein.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method for softening and/or disrupting calcium deposits within the intimal and medial layers of a wall of a biological lumen, comprising:

generating a series of circumferentially-delivered, pulsatile low-frequency forces against the conduit or lumen wall, the low-frequency forces sufficient to cause a deflection of the lumen wall and produce low-frequency energy waves within the intimal and medial layers of the lumen wall;

simultaneously generating a series of circumferentially-delivered, pulsatile high-frequency forces against the conduit or lumen wall, the high-frequency forces sufficient to cause a deflection of the lumen wall and produce high-frequency energy waves within the intimal and medial layers of the lumen wall, thereby creating a combination of low-frequency and high-frequency wall forces;

producing a resulting combination of low-frequency and high-frequency energy waves within the intimal and medial layers of the lumen wall;

thereby targeting a combination of low-frequency wall forces, high-frequency wall forces, low frequency energy waves and high-frequency energy waves to the intimal and medial layers of the wall of the lumen;

wherein the generated low-frequency and high-frequency forces comprise initial magnitudes that are increased at least once; and softening and/or disrupting the calcium deposits within the intimal and medial layers of the wall of the biological lumen as the generated low-frequency and high-frequency forces are increased.

2. The method of claim 1, wherein the low-frequency forces and the high-frequency forces are generated by mechanical and/or non-mechanical means.

3. The method of claim 1, wherein the combination of low-frequency forces, high-frequency forces, low-frequency energy waves and high-frequency energy waves disrupt the calcification within the intimal and medial layers.

4. The method of claim 3, wherein the softening and/or disrupting of the calcification increases the compliance of the intimal and medial layers of the biological conduit or lumen.

* * * * *